United States Patent [19]
Maschler

[11] Patent Number: 4,603,138
[45] Date of Patent: Jul. 29, 1986

[54] AMINE DERIVATIVES

[75] Inventor: Harald Maschler, Nordstemmen, Fed. Rep. of Germany

[73] Assignee: Beecham Wuelfing GmbH & Co. KG, Fed. Rep. of Germany

[21] Appl. No.: 502,673

[22] Filed: Jun. 9, 1983

[30] Foreign Application Priority Data

Jun. 10, 1982 [GB] United Kingdom ............... 8216911
Jun. 25, 1982 [GB] United Kingdom ............... 8218407
Mar. 15, 1983 [GB] United Kingdom ............... 8307081

[51] Int. Cl.$^4$ .................. A61K 31/445; C07D 211/58
[52] U.S. Cl. .................................. 514/329; 514/319; 514/821; 546/197; 546/205; 546/206; 546/223; 546/224; 546/193
[58] Field of Search ............... 424/267; 546/223, 205, 546/206, 224; 514/329, 319

[56] References Cited

U.S. PATENT DOCUMENTS

| | | | |
|---|---|---|---|
| 3,147,268 | 9/1964 | Meltzer | 548/530 X |
| 3,423,415 | 1/1969 | Jucker et al. | 546/223 |
| 3,531,487 | 9/1970 | Berger et al. | 546/223 X |
| 3,723,524 | 3/1973 | Augstein et al. | 546/223 X |
| 3,992,389 | 11/1976 | Cavalla | 546/223 X |
| 4,001,328 | 1/1977 | Molloy | 260/567.6 M |
| 4,206,117 | 6/1980 | Von Philipsborn et al. | 544/60 X |
| 4,379,167 | 4/1983 | Lunsford et al. | 564/349 X |
| 4,463,190 | 7/1984 | Lunsford et al. | 260/501.17 X |
| 4,499,100 | 2/1985 | Kluge et al. | 514/321 |

FOREIGN PATENT DOCUMENTS 2825961 1/1980 Fed. Rep. of Germany .
1457086 2/1975 United Kingdom .

OTHER PUBLICATIONS

Sadet, et al., Bull. Soc. Chem. Fr., (Part 2), 1973, No. 6, pp. 2016-2029.

Primary Examiner—Joseph Paul Brust
Attorney, Agent, or Firm—Jacobs & Jacobs

[57] ABSTRACT

Compounds of the formula (I):

$$Ar-E-CHR_5-J-N\begin{pmatrix}R_4\\ \end{pmatrix}N-R_1 \quad (I)$$

and pharmaceutically acceptable acid addition salts thereof, wherein,

Ar is optionally substituted phenyl or naphthyl, or pyridyl;

E is O, S or a bond;

$R_5$ is hydrogen, and

J is $C_{3-5}$ polymethylene, optionally substituted by one or two groups selected from methyl or optionally derivatized hydroxy; or Ar and $R_5$ together form a group $$Ar^1\begin{pmatrix}Z\\ \end{pmatrix}(CH_2)_m$$

where $Ar^1$ is optionally substituted 1,2-phenylene;

Z is O or $CH_2$, and m is 0 or 1, when E is O or S, or 1 when E is bond;

$R_1$ is hydrogen, $C_{1-4}$ alkyl optionally substituted phenyl; $C_{3-8}$ alkanoyl, or phenyl $C_{2-8}$ alkanoyl, any phenyl moiety being optionally substituted; a group $COR_2$ where $R_2$ is $C_{2-3}$ alkoxy, phenyl $C_{1-4}$ alkoxy, the phenyl moiety being optionally substituted, or $C_{1-4}$ alkoxy $C_{3-4}$ alkoxy; or a group $CXNHR_3$ where X is O or S and $R_3$ is $C_{2-4}$ alkyl, $C_{2-4}$ alkenyl, phenyl or phenyl $C_{1-4}$ alkyl, any phenyl moiety being optionally substituted; and $R_4$ is hydrogen or $C_{1-4}$ alkyl, compositions containing them, and processes for their preparation.

9 Claims, No Drawings

AMINE DERIVATIVES

This invention relates to antiarrhythmic compounds, to pharmaceutical compositions containing them, and to processes for their preparation.

A class of compounds with antiarrhythmic activity but minimal β-blocking effects on the heart or bronchioles has been found.

The present invention provides the compounds of the formula (I):

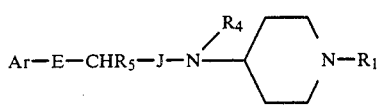

and pharmaceutically acceptable acid addition salts thereof,
wherein,
E is O, S or a bond; and
J is $C_{3-5}$ polymethylene, optionally substituted by one or two groups selected from methyl or optionally derivatised hydroxy and either Ar is optionally substituted phenyl or naphthyl, or pyridyl and $R_5$ is hydrogen; or
Ar and $R_5$ together form a group

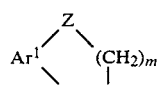

where
$Ar^1$ is optionally substituted 1,2-phenylene;
Z is O or $CH_2$, and
m is 0 or 1, when E is O or S, or 1 when E is a bond;
$R_1$ is hydrogen, $C_{1-4}$ alkyl or optionally substituted phenyl; $C_{3-8}$ alkanoyl, or phenyl $C_{2-8}$ alkanoyl, any phenyl moiety being optionally substituted; a group $COR_2$ where $R_2$ is $C_{2-3}$ alkoxy, phenyl $C_{1-4}$ alkoxy, the phenyl moiety being optionally substituted, or $C_{1-4}$ alkoxy $C_{3-4}$ alkoxy; or a group $CXNHR_3$ where X is O or S and $R_3$ is $C_{2-4}$ alkyl, $C_{2-4}$ alkenyl, phenyl or phenyl $C_{1-4}$ alkyl, any phenyl moiety being optionally substituted; and $R_4$ is hydrogen or $C_{1-4}$ alkyl.

When used herein 'optionally substituted' means optionally substituted by one or two substituents chosen from halogen, $C_{1-4}$ alkyl, $C_{1-4}$ alkoxy, $C_{2-7}$ acyloxy, cyano or trifluoromethyl. When used herein the term '$C_{2-7}$ acyloxy' is restricted to unsubstituted $C_{1-6}$ hydrocarbylcarboxy.

Ar is preferably unsubstituted. When Ar is substituted as defined, suitable substituents include fluorine, chlorine, methyl, methoxy, cyano and trifluoromethyl. A preferred value of Ar is phenyl.

E may be O, S or a bond. Often E is O.

$Ar^1$ is preferably unsubstituted. When $Ar^1$ is substituted as defined, suitable substituents include fluorine, chlorine, methyl, methoxy, cyano and trifluoromethyl. A preferred value of Ar is 1,2-phenylene. E and Z are often each O and m is 0 or 1, preferably 1.

Suitable values of J include

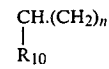

wherein n is 2 to 4 and $R_{10}$ is hydrogen, methyl or hydroxy or derivatised hydroxy. n is preferably 2 or 3.

Derivatised hydroxy $R_{10}$ include nitrato; $C_{1-4}$ alkoxy, in particular methoxy; phenyl $C_{1-4}$ alkoxy, in particular benzyloxy; and $C_{1-7}$ carboxylic acyloxy, such as $C_{1-4}$ alkanoyloxy, in particular acetoxy. $R_{10}$ is preferably hydroxy.

Examples of $C_{1-4}$ alkyl for or within $R_1$ and $R_{10}$ and for $R_4$ include methyl, ethyl, n- and iso-propyl and n-, and tert-butyl, often methyl, ethyl, n-propyl, or n-butyl. Favoured $C_{1-4}$ alkyl include ethyl and n-propyl.

Examples of $C_{2-4}$ alkenyl within $R_1$ include vinyl, allyl and E and Z prop-1-enyl.

Examples of $C_{3-8}$ alkanoyl for or within $R_1$ include propionyl, n- and iso-butyryl,2,2-dimethylpropanoyl (pivaloyl) and n-valeryl, preferably n-butyryl and n-valeryl. Examples of $C_{2-8}$ alkanoyl in $R_1$ optionally substituted phenyl $C_{2-8}$ alkanoyl include the above examples of $C_{3-8}$ alkanoyl and acetyl. Examples of $C_{1-4}$ alkanoyl for $R_{10}$ include appropriate of the foregoing and acetyl.

Optionally substituted phenyl within $R_1$ is often unsubstituted.

Examples of $C_{1-4}$ alkoxy within $R_1$ include methoxy, ethoxy and n- and iso-propoxy.

From the foregoing it will be appreciated that suitable $R_1$ groups include methyl, ethyl and n-propyl; optionally substituted phenyl; propionyl, n and iso-butyryl and 2,2-dimethylpropanoyl (pivaloyl); ethoxycarbonyl, n- and iso-propoxycarbonyl; optionally substituted benzyloxycarbonyl and phenylpropoxycarbonyl; 3-methoxypropoxycarbonyl; ethylcarbamoyl, n- and iso-propylcarbamoyl, n- and tert-butylcarbamoyl, vinylcarbamoyl, allylcarbamoyl, E- and Z- prop-2-enylcarbamoyl, optionally substituted phenylcarbamoyl, optionally substituted benzylcarbamoyl, and phenethylcarbamoyl; ethylthiocarbamoyl, n- and iso-propylthiocarbamoyl, n- and tert-butylthiocarbamoyl, phenylthiocarbamoyl, benzylthiocarbamoyl, vinyl-thiocarbamoyl, allylthiocarbamoyl and E- and Z- prop-2-enylthiocarbamoyl.

A value of $R_1$ of interest is n-butylcarbamoyl. Favoured $R_1$ include n-butyryl, n-valeryl, ethoxycarbonyl, n-propoxycarbonyl, n-propylcarbamoyl isopropylcarbamoyl and n-propylaminothiocarbonyl, in particular n-propylcarbamoyl.

The compounds of the formula (I) may contain an optical centre e.g. at the point of substitution by an $R_{10}$ optionally derivatised hydroxyl group or a methyl group. The compounds may thus be provided in R-form, S-form or in mixtures thereof such as the RS-form. The RS-form is particularly apt in view of its greater ease of synthesis. The invention extends to all isomers including enantiomers of the compounds of all formula (I) and to mixtures thereof including racemates.

It is preferred that the compounds of formula (I) are in substantially pure form.

The compounds of the formula (I) may also form solvates and the invention extends to such solvates.

The compounds of the formula (I) may form acid addition salts at the $NR_4$ nitrogen atom, and at the $NR_1$ nitrogen atom when it is a non-amidic nitrogen atom.

The pharmaceutically acceptable salts of the compounds of the formula (I) include acid addition salts with conventional acids such as hydrochloric, hydrobromic, phosphoric, sulphuric, citric, tartaric, lactic and acetic acids.

The salts of the compounds of the formula (I) also include quaternary ammonium salts. Examples of such salts include such compounds quaternised by compounds such as $R_7$—Y wherein $R_7$ is $C_{1-6}$ alkyl, phenyl—$C_{1-6}$ alkyl or $C_{5-7}$ cycloalkyl, and Y is an anion of an acid. Suitable examples of $R_7$ include methyl, ethyl and n- and iso-propyl; and benzyl and phenylethyl. Suitable examples of Y include the halides such as chloride, bromide and iodide.

Crystalline acid addition salts are favoured in view of their enhanced stability. Crystalline salts may be solvated, for example hydrated.

A group of compounds of formula (I) is of formula (IA):

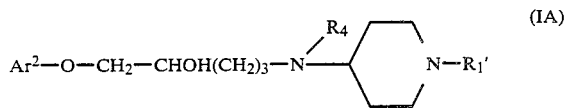
(IA)

and pharmaceutically acceptable acid addition salts thereof,
wherein
$Ar^2$ is optionally substituted phenyl or naphthyl, or pyridyl;
$R_1'$ is $C_{1-4}$ alkyl or optionally substituted phenyl; $C_{3-6}$ alkanoyl, benzoyl or phenyl $C_{2-6}$ alkanoyl, any phenyl moiety being optionally substituted, a group $COR_2$ where $R_2$ is $C_{2-3}$ alkoxy, phenyl $C_{1-4}$ alkoxy, the phenyl moiety being optionally substituted, or $C_{1-4}$ alkoxy $C_{3-4}$ alkoxy; or a group $CXNHR_3$ where X is O or S and $R_3$ is $C_{2-4}$ alkyl, $C_{2-4}$ alkenyl, phenyl or phenyl $C_{1-4}$ alkyl, any phenyl moiety being optionally substituted; and $R_4$ is hydrogen or $C_{1-4}$ alkyl.

A second group of compounds of formula (I) is of formula (IB):

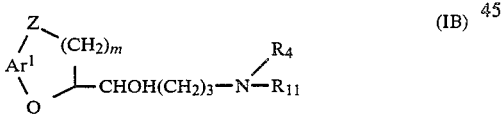
(IB)

and pharmaceutically acceptable acid addition salts thereof,
wherein
$Ar^1$ is optionally substituted 1,2-phenylene;
Z is O or $CH_2$;
m is O or 1;
$R_{11}$ is a group $N$-$R_1''$-4-piperidyl where $R_1$ is $C_{1-4}$ alkyl or optionally substituted phenyl; $C_{3-6}$ alkanoyl, or phenyl $C_{2-6}$ alkanoyl, any phenyl moiety being optionally substituted; a group $COR_2$ where $R_2$ is $C_{2-3}$ alkoxy, phenyl $C_{1-4}$ alkoxy, the phenyl moiety being optionally substituted, or $C_{1-4}$ alkoxy $C_{3-4}$ alkoxy; or a group $CXNHR_3$ where X is O or S and $R_3$ is $C_{2-4}$ alkyl, $C_{2-4}$ alkenyl, phenyl or phenyl $C_{1-4}$ alkyl, any phenyl moiety being optionally substituted; and $R_4$ is hydrogen or $C_{1-4}$ alkyl.

Another group of compounds within formula (I) is of formula (II):

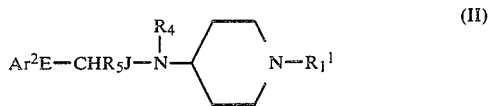
(II)

wherein
$Ar^2$ is optionally substituted phenyl or naphthyl or pyridyl;
$R_1^1$ is $C_{3-8}$ alkanoyl or optionally substituted phenyl $C_{2-8}$ alkanoyl; and
E, J, $R_4$ and $R_5$ are as defined in formula (I).

Suitable, favoured and preferred variables are as so described for corresponding variables under formula (I).

A further group of compounds within formula (I) is of formula (III):

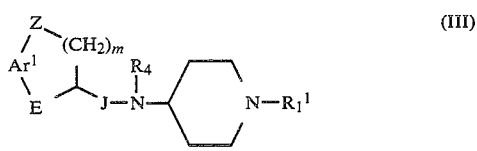
(III)

wherein the variables are as defined in formulae (I) and (II).

Suitable, favoured and preferred variables are as so described for corresponding variables under formula (I).

Another group of compounds within formula (I) is of formula (IV):

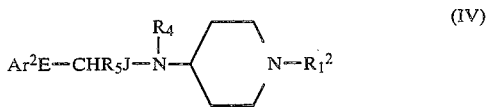
(IV)

wherein
$R_1^2$ is a group $COR_2$ where $R_2$ is $C_{2-3}$ alkoxy, phenyl $C_{1-4}$ alkoxy, the phenyl moiety being optionally substituted, or $C_{1-4}$ alkoxy $C_{3-4}$ alkoxy; or a group $CXNHR_3$ where X is O or S and $R_3$ is $C_{2-4}$ alkyl, $C_{2-4}$ alkenyl, phenyl or phenyl $C_{1-4}$ alkyl, any phenyl moiety being optionally substituted; and the remaining variables are as defined in formula (II).

Suitable, favoured and preferred variables are as so described for corresponding variables under formula (I).

A further group of compounds within formula (I) is of formula (V):

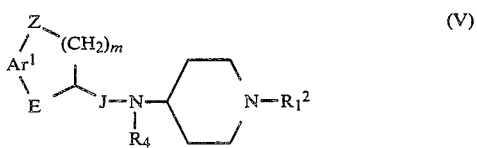
(V)

wherein the variables are as defined in formulae (I) and (IV).

Suitable, favoured and preferred variables are as so described for corresponding variables under formula (I).

A group of compounds of interest is of formula (VI):

$$\text{(VI)} \quad \underset{\text{OH}}{\underset{|}{\text{R}_6\text{-C}_6\text{H}_4\text{-O-CH}_2\text{-CH-(CH}_2)_n\text{-NH-}}}\underset{}{\text{piperidine}}\text{-N-R}_1$$

wherein:
n and $R_1$ are as defined in and under formula (I); and
$R_6$ is hydrogen, $C_{1-4}$ alkyl, $C_{1-4}$ alkoxy, $C_{2-7}$ acyloxy, cyano or trifluoromethyl.

Suitable and favoured and preferred $R_1$ and $R_6$ are so described under formula (I).

A group of compounds within formula (VI) is formula (VII):

$$\text{(VII)} \quad \underset{\text{OH}}{\underset{|}{\text{PhOCH}_2.\text{CH(CH}_2)_n\text{-NH-}}}\underset{}{\text{piperidine}}\text{-N-R}_1^3$$

wherein
n is 2, 3 or 4; and
$R_1^3$ is $C_{3-8}$ alkanoyl, $C_{2-3}$ alkoxycarbonyl, or $\text{CXNHR}_3^1$ where X is O or S, and $R_3^1$ is $C_{3-4}$ alkyl.

Suitable, favoured and preferred $R_1^3$ are as so described for corresponding variables under formula (I).

A second group of compounds within formula (VII) is of formula (VIII):

$$\text{(VIII)} \quad \underset{\text{OH}}{\underset{|}{\text{PhOCH}_2.\text{CH.(CH}_2)_{n^1}\text{-NH-}}}\underset{}{\text{piperidine}}\text{-N-CXNHR}_3^1$$

wherein $R_3^1$ is as defined in formula (VII), and $n^1$ is 2 or 3.

$n^1$ is preferably 3
$R_3^1$ is preferably n-propyl.

The present invention also provides a process for the preparation of a compound of the formula (II) whch process comprises the reaction of the compounds of the formulae (IX) and (X):

$$\text{Ar-E-L} \quad \underset{Y}{\overset{X}{\text{piperidine}}}\text{N-R}_9$$
$$\text{(IX)} \quad \text{(X)}$$

wherein
$R_9$ is $R_1$ as defined or benzyl optionally substituted in the phenyl ring;

(i)
(a) L is $\text{CHR}_5\text{JNH}_2$ and X and Y together are oxo;
(b) L is $\text{CHR}_5\text{J}^1\text{CHO}$ or $\text{CHR}_5\text{J}^2\text{COCH}_3$ where $J^1$ is $C_{2-4}$ polymethylene optionally substituted by one or two groups selected from methyl or optionally derivatised or protected hydroxy, and $J^2$ is $C_{2-4}$ polymethylene optionally substituted by a methyl or optionally derivatised or protected hydroxy group, X is $\text{NH}_2$ and Y is H;

(ii)
(a) L is $\text{CHR}_5\text{J}^3\text{Q}_1$ or $\text{CHR}_5\text{J}^1\text{COQ}_2$ where $J^3$ is J with any hydroxy group protected and $Q_1$ and $Q_2$ each are a group readily displaceable by a nucleophile, X is $\text{NHR}_4$ and Y is H;
(b) L is $\text{CHR}_5\text{J}^3\text{NHR}_4$, X is $Q_1$ and Y is H; or
(c) E is O or S, L is H or an alkali metal atom, X is $\text{Q}_3\text{CHR}_5\text{-J}^3\text{-NR}_4$ where $Q_3$ is a group readily displaceable by a nucelophile and Y is H;

(iii)
(a) L is $\text{CHR}_5\text{J}^4\text{CHO}$ or $\text{CHR}_5\text{J}^5\text{COCH}_3$ where $J^4$ is a bond or $C_{1-2}$ polymethylene optionally substituted by a methyl or protected or derivatised hydroxy group and $J^5$ is a bond or $C_{1-2}$ polymethylene, Y is H and X is $M_1J^6\text{NR}_{12}$ where $J^6$ is $C_{1-4}$ polymethylene determined by $J^4$ or $J^5$ and optionally substituted by a methyl or derivatised hydroxy group when $J^4$ is unsubstituted, $M_1$ is a lithium (I) or halomagnesium (II) group and $R_{12}$ is an N-protecting group; or
(b) L is $\text{CHR}_5\text{J}^4\text{M}_1$ or $\text{CHR}_5\text{J}^5\text{CHM}_1.\text{CH}_3$, Y is H and X is $\text{CHO.J}^6\text{NR}_{12}$;

(iv)
(a) L is $$\text{CHR}_5.\text{J}^7\text{-}\underset{O}{\triangle}$$

wherein $J^7$ is $C_{1-3}$ polymethylene optionally substituted by a methyl or protected or derivatised hydroxy group, Y is H and X is $\text{NHR}_4$; or
(b) E is O or S, L is H or an alkali metal atom, Y is H and X is $$\underset{O}{\triangle}\text{-J}^7\text{NR}_4;$$

or
(V) ArEL is $$\text{Ar}'\underset{\text{E}'\text{L}_1}{\overset{\text{Z}'\text{L}_2}{<}}$$

where Z' is O and E' is O or S and $L_1$ and $L_2$ are each H or an alkali metal atom, Y is H and X is $$\underset{Q_5}{\underset{|}{\text{Q}_4(\text{CH}_2)_m\text{CH.JNR}_4}}$$

wherein $Q_4$ and $Q_5$ are each independently a group readily displaceable by a nucleophile;
and thereafter as necessary reducing the resulting compound, or in the resulting compound converting $R_9$ benzyl to $R_1$, deprotecting any protected hydroxy group, converting $R_{12}$ to hydrogen, optionally converting $R_1$ or $R_4$ to other $R_1$ or $R_4$ and optionally salifying the resultant compound of formula (I).

Suitable examples of $Q_1$, $Q_3$ $Q_4$ and $Q_5$ include halide such as Cl, or I or labile acyloxy groups such as $\text{OSO}_2\text{CH}_3$ and $\text{OSO}_2.\text{C}_6.\text{H}_4.\text{p-CH}_3$. Suitable examples of $Q_2$ include halide such as Cl or Br, acyloxy such as $C_{1-4}$ alkanoyloxy, and hydroxy.

Suitable examples of L alkali metal atoms include sodium and potassium.

It will be appreciated by the skilled man that a protected hydroxyl group is a conventional group readily convertible after a desired reaction to a hydroxyl group. An $R_{12}$ N-protecting group is a conventional group similarly readily removable.

Examples of protected hydroxyl include $C_{1-4}$ alkoxy and $C_{2-7}$ acyloxy as defined and described in and under formula (I), benzyloxy optionally substituted in the phenyl ring by one or two substituents selected from $C_{1-4}$ alkyl, $C_{1-4}$ alkoxy, trifluoromethyl, halogen or nitro; and tetrahydropyranyloxy.

Examples of $R_{12}$ N-protecting groups include benzyl optionally substituted as for benzyloxy above.

In process variant (i), the condensation of the compounds of the formulae (IX) and (X) is conveniently effected at non-extreme temperatures at about ambient, in a dry inert polar solvent, such as dry methanol.

As the condensation eliminates water, it is preferable to carry out the reaction in the presence of a dehydrating agent, for example molecular sieves.

The use of a non-aqeous acid catalyst can be advantageous, for example hydrogen chloride or p-toluenesulphonic acid, or alternatively an acid addition salt of the compound of formulae (IX) or (X) containing the amino function.

The product compound must be reduced to give a compound of formula (I). This is conveniently effected in situ, and most conveniently simultaneously with the condensation.

The reduction of the product compound is conveniently simultaneously effected with a mild reducing agent, such as a mild inorganic complex hydride, for example sodium cyanoborohydride.

If a mild inorganic complex hydride reductant is used, the reaction is generally carried out in a dry, inert polar solvent, such as dry ethanol, maintained at neutral or acid pH, for example pH 5-7, with for example hydrogen chloride with pH less than 7.

Non-extreme temperatures at about ambient are generally suitable.

Alternatively, the reduction may be effected sequentially, optionally with isolation of the condensation product and conventional transition-metal catalysed hydrogenation may be employed, using for example palladium—or platinum—charcoal, at atmospheric pressure or a slight excess thereover. The above solvents and temperatures are apt.

In variants (ii) and (v), reaction is generally effected in an inert solvent, at a non extreme temperature, for example solvent reflux temperature. The presence of an acid acceptor, such as potassium carbonate or an appropriate organic base is often advantageous.

When L is $CHR_5J^1COQ_2$, $Q_2$ may be hydroxyl, when reaction may be effected in the presence of a dehydrating agent such as dicyclohexylcarbodiimide.

Subsequent reduction of the carbonyl function may be effected by using a strong reductant such as lithium aluminium hydride.

Alternatively, the reduction in variant (i) may be carried out concomitantly by effecting reductive alkylation for example using $L=CHR_5J^1CHO$ in the presence of an inorganic hydride reductant such as sodium borohydride.

In variant (ii) (c) reaction is generally effected in the presence of a strong base which, if L is H, often convertes it in situ to an alkali metal atom.

In variant (iii), where M is a magnesium (II) halide group, the compound of formula (IX) or X may be prepared in situ under conventional conditions for Grignard reagents. Those are: reaction of the halide, preferably the bromide, corresponding to the compound of formula (IX) or (X) with a molar equivalent or excess of dry, grease-free magnesium particles in a dry ether, for example THF, dimethoxyethane or diethyl ether, free of protic solvents. THF is a preferred solvent. The presence of trace quantities of dibromoethane may be advantageous. Ambient and non-extreme depressed temperatures are suitable, for example between ambient and $-15°$ C., although gentle initiative heating may be advantageous.

When M is lithium, the compound of formula (IX) or (X) may be prepared in situ under conventional indirect metallation conditions, for example by reaction of the above corresponding halide, preferably the bromide with n-butyl lithium. Temperatures of ambient to $-60°$ C. are suitable. The completed reaction is conveniently quenched with water.

In varient (iv) reaction is normally carried out in an inert solvent, for example an ether such as diethyl or diisopropyl ether at solvent reflux temperature. The reaction proceeds well in the presence of a strong inorganic base, such as sodium amide.

As regards the subsequent reaction steps:

When protected hydroxy is of the form $R_{13}O$ where $R_{13}$ is $C_{1-4}$ alkyl, conversion is conveniently effected by conventional methods, such as by boron tribromide or boron triiodide or iodotrimethylsilane. Warm aqueous hydrobromic acid or pyridine hydrochloric may also be used.

When $R_{13}$ is $C_{2-6}$ alkanoyl or benzoyl optionally substituted as defined deprotection may be effected convnetionally, for example by acidic or basic hydrolysis.

When $R_{13}$ is optionally substituted benzyl as defined above, or tetrahydropranyl, conversion is conveniently effected by conventional methods such as transition metal catalysed hydrogenolysis, using for example palladium or platinum-charcoal, at about atmospheric pressure. Non-extreme temperatures at about ambient are generally suitable.

Hydroxy and derivatised hydroxy may be interconverted by conventional etherification deetherification, esterification and deesterification reactions, as appropriate.

When $R_{12}$ is optionally substituted benzyl as defined, conversion to hydrogen may be carried out conventionally, for example by hydrogenolysis. Suitable reaction conditions are as so described for $R_{10}$ hydrogenolysis.

$R_1$ groups will not generally be interconverted but those which correspond to $R_{12}$ groups as defined may be removed as described for $R_{12}$, and the resulting amine function conventionally acylated, alkylated reductively alkylated or treated with a corresponding iso(thio)cyanate to introduce $R_1$.

$R_1$ groups will generally be interconverted in the precursor intermediates to the compounds of formula (X).

Suitable alkylating or acylating agents in both cases will have the form $R_1Q_2$ where $Q_2$ is a group readily displaceable by a nucelophile.

Suitable $Q_2$ when $R_1$ is alkyl are as noted above for Q and $Q_1$.

When $R_1$ is acyl, suitable $Q_2$ include halo, hydroxy and $C_{1-4}$ alkoxy, in particular halo.

Reaction is normally effected, when $R_1$ is $C_{1-4}$ alkyl, as for N-alkylation in the main process.

When $R_1$ is acyl, reaction is usually effected without solvent if both reagents are liquid at room temperature, or otherwise in an inert solvent such as toluene or diethyl ether, usually at room temperature. As noted for main-process acylation, the presence of an acid acceptor, especially when $Q_2$ is halo is preferred.

When $R_1$ is of the formula $CXNHR_3$ as defined acylation is generally effected using the corresponding iso(thio)cyanate $XCN.R_3$, under conventional conditions for urethane formation.

$R_4$ hydrogen is conveniently converted to $R_4$ $C_{1-4}$ alkyl by reductive alkylation, for example by reaction of the compound of the formula (I) with the corresponding $C_{1-4}$ alkanaldehyde in the presence of an inorganic hydride reductant such as sodium borohydride.

Conversion to $R_4$ methyl may be effected with formaldehyde in the presence of a mild reductant such as sodium cyanoborohydride in an inert highly polar solvent such as acetonitrile.

It will, of course, be appreciated that all the foregoing conversions may also be effected on corresponding variables in corresponding intermediates which are not of formula (I), as appropriate under any given reaction conditions.

From the aforegoing it will be appreciated that this invention also provides a second process for the preparation of a compound of the formula (I) or a pharmaceutically acceptable salt thereof, which process comprises the de-protection of a compound of the formula (XI).

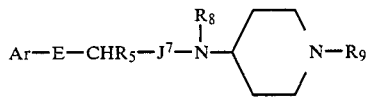
(XI)

wherein $J^7$ is J or J in which any hydroxyl function is protected; $R_8$ is $R_4$ as defined or an N-protecting group; and $R_9$ is as defined with the proviso that at least one of $J^7$, $R_8$ and $R_9$ contains protected hydroxyl or is an N-protecting group respectively, and therafter, as necessary in the resultant compound converting $R_1$ or $R_4$ to other $R_1$ or $R_4$, and optionally salifying the resultant compound of formula (I).

Suitable process conditions are as so described for the relevant first process steps hereinbefore.

The invention also provides a process for the preparation of a compound of the formula (I), which process comprises the reduction of a compound of the formula (XII):

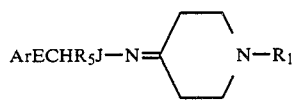
(XII)

in tautomerism with the form of formula (XIII)

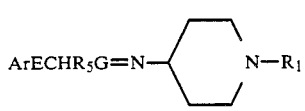
(XIII)

wherein G is the trivalent analogue of J, and the remaining variables are as defined in formula (I).

Suitable process conditions are as so described for the relevant first process steps hereinbefore.

The acid addition salts of compounds of formula (I) may be prepared in entirely conventional manner by reacting a compound of the formula (I) in base form with the chosen acid.

The quaternary ammonium salts of the compounds of the formula (I) may be prepared in conventional manner for such salts, such as by reaction of the chosen compound of the formula (I) with a compound $R_7Y$ as defined. This reaction is suitable carried out in an appropriate solvent such as acetone, methanol, ethanol, dimethylformamide and the like, at ambient or raised temperature and pressure.

The invention also provides a pharmaceutical composition comprising a compound of the formula (I), or a pharmaceutically acceptable salt thereof, together with a pharmaceutically acceptable carrier.

Such compositions may be adapted for oral or parenteral administration, and as such may be in the form of tablets, capsules, oral liquid preparations, powders, granules, lozenges, reconsitutable powders, injectable and infusable solutions or suspensions the compositions may also be in the form of suppositories. Normally, orally administrable compositions are preferred.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups or elixirs or may be presented in a dry product for reconstitution with water or other suitable vehicle before use. Such liquid preparations may contain conventional additives such as suspending agents, emulsifying agents, non-aqueous vehicles (whcih may include edible oils), preservatives, and if desired conventional flavouring or colouring agents, and the like.

For parenteral administration, fluid unit dosage forms are prepared utilizing the compound of the formula (I) and a sterile vehcile. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle.

Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the compound.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention provides a compound of formula (I) for the treatment or prophylaxis of cardiac arrhythmias.

The invention further provides a method of treatment or prophylaxis of cardiac arrythmias in mammals including humans comprising the administration to the sufferer of an effective amount of a compound of the formula (I) or a pharmaceutically acceptable salt thereof. The "effective amount" will depend in the usual way on a number of factors such as the nature and severity of the malady to be treated, the weight of the sufferer, and the actual compound used.

However, by way of illustration, unit doses will suitably contain 0.01 to 20 mg of the compound of formula (I), for example 0.02 to 10 mg, usually 5 to 10 mg.

The following Examples illustrate the preparation of compounds of formula (I), and the following Descriptions illustrate the preparation of intermediates thereof.

Satisfactory $^1$H n.m.r. data were obtained for all the following products.

DESCRIPTION 1

4-phenoxy-3-hydroxyvaleronitrile (D.1)

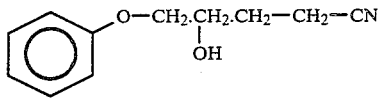

Acetonitrile (48 g) was added with stirring to a suspension of NaNH$_2$ (105 g) in dry diethyl ether (1.7l) over 0.5 hr, and the suspension was refluxed for a further 0.5 hr.

1-phenoxy-2,3-epoxypropane (180 g) was added, and the suspension was refluxed for 6 hr. with stirring under nitrogen. The mixture was cooled to room temperature and the yellow-brown precipitate was filtered off under suction, washed with diethyl ether (×4) and added to a stirred ice-diethyl ether mixture. The resulting ethereal solution of the precipitate was separated, and the aqueous phase further extracted with diethyl ether (×3).

The combined ether extracts were extracted with M HCl washed to neutral with water, dried (Na$_2$SO$_4$), filtered and the solvent was removed in vacuo, yielding (D.1) (132 g, 58%) as a pale yellow oil which crystallised in the refridgerator, used subsequently without further purification.

| Analysis: | C | H | N | O |
|---|---|---|---|---|
| calc. for C$_{11}$H$_{13}$NO$_2$ | 69.09 | 6.85 | 7.32 | 16.73 |
| found | 69.06 | 6.83 | 7.31 | 16.68 |

DESCRIPTION 2

5-phenoxypentan-4-ol-1-amine (D.2)

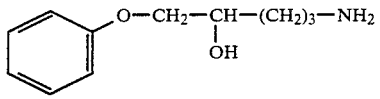

Nitrile (D.1) (132 g) in diethyl ether (600 ml) was added dropwise at 0° C. with vigorous stirring under nitrogen to LiAlH$_4$ (41 g) suspended in dry diethyl ether (1.8l). The mixture was then stirred for 2.5 hr. at room temperature and then refluxed for 20 min.

Excess LiAlH$_4$ was destroyed by dropwise addition of water. The ethereal phase was separated off, and the aqueous layer was extracted with diethyl ether. The combined ethereal extracts were dried (Na$_2$SO$_4$), filtered, and the solvent was removed in vacuo.

The oily residue was dissolved in M HCl, basified (M NaOH) to pH 11, and the solution extracted with diethyl ether (×3), and at pH 13 with dichloromethane (×3). The combined organic extracts were dried (Na$_2$SO$_4$) filtered and the solvent was removed in vacuo yielding (D.2) (86 g, 70%) as a colourless oil, crystallising on standing in the refrigerator.

m.pt. 39°-40° C.

| Analysis | C | H | N | O |
|---|---|---|---|---|
| calc. for C$_{11}$H$_{17}$NO$_2$ | 67.66 | 8.78 | 7.17 | 16.39 |
| | 67.51 | 8.75 | 7.19 | 16.24 |

The following are prepared analogusly:

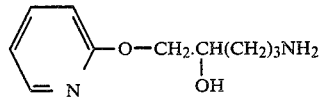

| No. | R |
|---|---|
| (D3) | 4-AcO |
| (D4) | 4-Cl |
| (D5) | 4-Me |

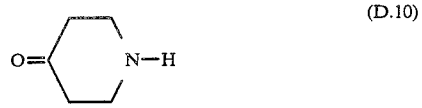

| No. | R |
|---|---|
| (D6) | H |
| (D7) | 4-Me |
| (D8) | 4-MeO. |

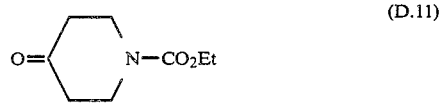
(D9)

DESCRIPTION 3

Piperid-4-one (D.10) (unstable)

(D.10)

Piperid-4-one hydrate hydrochloride (200 g) in water (800 ml) was neutralised with NaOH (47 g) in water (200 ml), and the solution extracted with chloroform (×4). The organic layer was dried (Na$_2$SO$_4$), filtered and used in solution.

DESCRIPTION 4

1-Ethoxycarbonylpiperid-4-one (D.11.)

(D.11)

(D.10) (10 g), ethyl chloroformate (12 g) and K$_2$CO$_3$ (14 g) were stirred together at room temperature for 40 hr under nitrogen.

The mixture was filtered, and filtrate solvent was removed in vacuo. The residue was treated with diethyl ether, filtered and the ether removed in vacuo yielding (D.11.) (12.4 g, 76%) as a pale yellow oil used without further purification.

The following were prepared analogously:

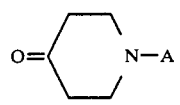

| No. | A |
|---|---|
| (D12) | CO—OPr$^n$ |
| (D13) | CO.O—CH$_2$Ph |
| (D14) | COEt |
| (D15) | COPr$^n$ |
| (D16) | COBu$^n$ |

The following are prepared analogously:

| No. | |
|---|---|
| (D17) | 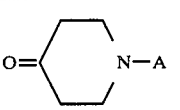 CO.O(CH$_2$)$_2$—〈 〉—Me |
| (D18) | COPr$^i$ |
| (D19) | 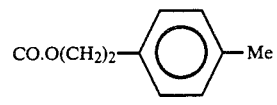 CO—〈 〉—CF$_3$ |
| (D20) | 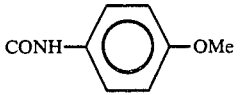 COCH$_2$—〈 〉—F |
| (D21) | 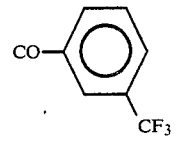 CO(CH$_2$)$_2$—〈 〉—F |
| (D22) | Pr$^n$ |
| (D23) | Ph |
| (D24) | 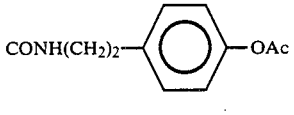 —〈 〉—CN |
| (D25) | CO$_2$Pr$^i$ |
| (D26) | Me |
| (D33) | CO$_2$(CH$_2$)$_3$OMe |
| (D49) | CO$_n$—C$_5$H$_{11}$ |
| (D50) | CO$_n$—C$_6$H$_{13}$ |
| (D51) | CO$_n$—C$_7$H$_{15}$ |

DESCRIPTION 5

1-Propylaminocarbonylpiperid-4-one (D.31)

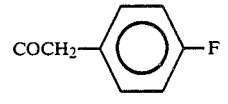

(D31) O=〈 〉N—CO.NH.Pr$^n$

To piperid-4-one (11.8 g) was added n-propyl isocyanate in small portions at room temperature with stirring. After stirring 48 hr the solvent was removed in vacuo, and the residue was treated with diethyl ether, yielding (D.31) (19.1 g, 86%) as a pale yellow oil.

The following were prepared analogously:

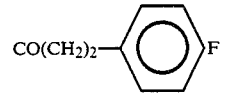

| No. | A |
|---|---|
| (D28) | CONHBu$^n$ |
| (D29) | CONHPh |
| (D30) | CONHEt |
| (D31) | CONHPr$^i$ |
| (D32) | CSNHPr$^n$ |

The following are prepared analogously:

| No. | A |
|---|---|
| (D34) | CONHBu$^t$ |
| (D35) | CONH.CH:CH$_2$ |
| (D36) | CONH.CH:CH.CH$_3$ |
| (D37) | CONH—〈 〉—OMe 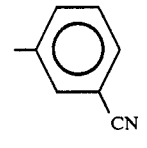 |
| (D38) | CONHCH$_2$Ph |
| (D39) | CONH(CH$_2$)$_2$—〈 〉—OAc 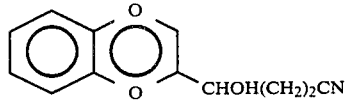 |
| (D40) | CSNHEt |
| (D41) | CSNHPr$^n$ |
| (D42) | CSNHPr$^i$ |
| (D43) | CSNHBu$^n$ |
| (D44) | CSNHBu$^t$ |
| (D45) | CSNHPh |
| (D46) | CSNHCH$_2$Ph |
| (D47) | CSNH.CH:CH$_2$ |
| (D48) | CSNH.CH$_2$CH:CH$_2$ |

DESCRIPTION 6

4-[2-(2,3-dihydrobenzo-1,4-dioxinyl)]-4-hydroxybutyronitrile

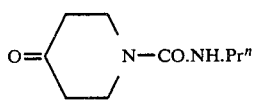 CHOH(CH$_2$)$_2$CN (D52)

Disodium catechol was reacted with 3,4-dichloro-1,2-expoxybutane by the method of U.S. Pat. No. 4,212,808, to give 2-(1,2-expoxyethyl)-2,3-dihydrobenzo-1,4-dioxin.

Acetonitrile (52 g) was added with stirring to a suspendion of NaNH$_2$(23 g) in dry diethyl ether (350 ml) over 0.5 hr, and the suspension was refluxed for a further 0.5 hr.

2-(1,2-epoxyethyl)-2,3-dihydrobenzo-1,4-dioxin (25 g) was added, and the suspension was refluxed for 6 hr. with stirring under nitrogen. The mixture was cooled to room temperature and the yellow-brown precipitate was filtered off under suction, washed with diethyl ether (×4) and added to a stirred ice-diethyl ether mixture.

DESCRIPTION 7

The following are prepared analogously to Description 4.

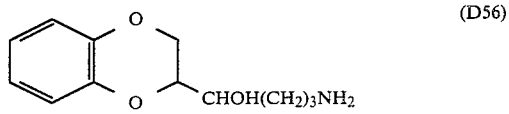

| No. | A |
|---|---|
| (D53) | —⟨⟩—Me |
| (D54) | COCH₂Ph |

DESCRIPTION 8

4-[2-(2,3-dihydrobenzo-1,4-dioxinyl)]-4-hydroxybutylamine (D56)

(D56)

Nitrile (D.1) (15 g) in diethyl ether (100 ml) was added dropwise at 0° C. with vigorous stirring under nitrogen to LiAlH₄ (4.8 g) suspended in dry diethyl ether (200 ml). The mixture was then stirred for 2.5 hr at room temperature and then refluxed for 20 min.

Excess LiAlH₄ was destroyed by dropwise addition of water. The ethereal phase was separated off, and the aqueous layer was extracted with diethyl ether. The combined ethereal extracts were dried (Na₂SO₄), filtered, and the solvent was removed in vacuo.

The oily residue was dissolved in M HCl, basified (M NaOH) to pH 11, and the solution extracted with diethyl ether (×3) and at pH 13 with dichloromethane (×3). The combined organic extracts were dried (Na₂SO₄) filtered and the solvent was removed in vacuo to minimum solution volume.

The solution was eluted down a silica gel column (chloroform methanol, 3:1) yielding (1) (8 g, 51%) as an oil crystallising on standing in the refrigerator.

| Analysis | C | H | N | O |
|---|---|---|---|---|
| calc. for C₁₂H₁₇NO₃ | 64.55 | 7.67 | 6.30 | 21.49 |
| found: | 64.30 | 7.49 | 6.70 | 21.45 |

The following are prepared analoguously:

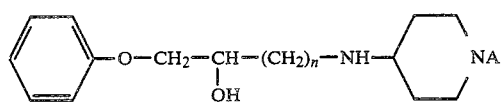

| No. | R |
|---|---|
| (D57) | 6-Et |
| (D58) | 6-Cl |

-continued

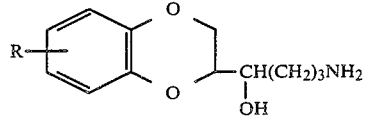

| No. | R |
|---|---|
| (D59) | 6-Me |

EXAMPLE 1

4-(5-phenoxy-4'-hydroxypentylamino)-1-ethoxycarbonylpiperidine

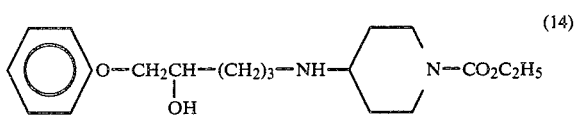
(14)

(D.2) (27 g) was dissolved in dry methanol (110 ml), and the solution neutralised to pH 7 by adding ethanolic HCl solution and cooled to room temperature. After adding 1-ethoxycarbonylpiperid-4-one (44 g), NaCNBH₃ (6 g) was added to the mixture under cooling and stiring, under nitrogen. After 0.5 hr, 3 Å molecular sieves were added and the mixture stirred at room temperature for 16 hr.

The resulting precipitate was filtered off under suction, washed with methanol, and the filtrate solvent was removed in vacuo.

The oily residue was extracted with diethyl ether at pH 7, and the aqueous layer at pH 14, was extracted twice with chloroform and washed with water.

After drying (Na₂SO₄) the extract was filtered and evaporated to dryness in vacuo crystallisation from diethyl ether yielded (1) (31 g, 70%) as colourless crystals.

m. pt. 86°–88° C.

| Analysis | | | | |
|---|---|---|---|---|
| Calc. for C₁₉H₂₃N₂O₄ | 65.12 | 8.63 | 7.99 | 18.26 |
| found | 65.08 | 8.66 | 7.95 | 18.25 |

The compounds of Table 1A, Table 1B and 1C were prepared analogously.

The compounds of Table 2 are prepared analogously.

TABLE 1A

⟨⟩—O—CH₂—CH(OH)—(CH₂)ₙ—NH—NA

| No. | A | n | % increase of voltage electro stimulation test dose 32 mg/kg i.d., 6 guinea pigs. |
|---|---|---|---|
| 1 | —C(=O)OC₂H₅ | 3 | 47,7* |

TABLE 1A-continued

Ph—O—CH₂—CH(OH)—(CH₂)ₙ—NH—[piperidine]—NA

| No. | A | n | % increase of voltage electro stimulation test dose 32 mg/kg i.d., 6 guinea pigs. |
|---|---|---|---|
| 2 | —CO—C₃H₇ⁿ | 3 | 50,8* |
| 3 | COBuⁿ | 3 | 83* |
| 4 | —CO—NH—C₂H₅ | 3 | 18,5* |
| 5 | —CO—NH—C₃H₇ⁿ | 3 | 77,8*+ |
| 6 | CONHPrⁱ | 3 | 58* |
| 7 | CSNHPrⁿ | 3 | 109* |
| 8 | CONHPrⁿ | 2 | 80,9*+ |
| 9 | CONHPrⁿ | 4 | 75* |
| 10 | CONHPrⁱ | 2 | 28* |
| 11 | —CO—NH—C₄H₉ⁿ | 3 | 66.7* (8 mg/kg) |
| 12 | —CO—NH—Ph | 3 | — |
| 13 | —CH₃ | 3 | 18,8* |
| 14 | —CO—OCH₂—CH₃ | 3 | 56,1* |
| 15 | —CO—O—CH₂CH₂—CH₃ | 3 | — |
| 16 | —CO—O—CH₂—Ph | 3 | 25,4* |

+ 30 mg/kg i.d.

TABLE 1B

Naphthyl—O—CH₂—CH(OH)(CH₂)₃—NH—[piperidine]—NA

| No. | A | % increase of voltage electro stimulation test dose 32 mg/kg i.d. 6 guinea pigs. |
|---|---|---|
| 17 | CO₂Et | 23* |

TABLE 1C

Ph—E(CH₂)ₚNH—[piperidine]—NA

| No. | E | A | p | % increase of voltage electro stimulation test dose 32 mg/kg i.d. 6 guinea pigs |
|---|---|---|---|---|
| 18 | — | CONHPrⁿ | 4 | 12.1* |
| 19 | O | CO₂Et | 5 | 29.4* |
| 20 | O | CONHPrⁿ | 5 | 29* |
| 21 | O | CSNHPrⁿ | 5 | 11* |
| 53 | — | CONHPrⁿ | 3 | 33* |

TABLE 2

R—Ph—O—CH₂CHOH(CH₂)₃—NH—[piperidine]—NA

| No. | R | A | No. | R | A |
|---|---|---|---|---|---|
| 22 | H | Prⁿ | 38 | H | CONH—Ph—OMe |
| 23 | H | Ph | 39 | H | CONHCH₂Ph |

TABLE 2-continued $$R \underset{}{\overset{}{\text{—}}} \text{phenyl} - O - CH_2CHOH(CH_2)_3 - NH - \text{piperidine} - NA$$

| No. | R | A | No. | R | A |
|-----|------|------|-----|------|------|
| 24 | H | 3-CN-phenyl | 40 | H | $CONH(CH_2)_2$-phenyl-OAC |
| 25 | H | $COPr^i$ | 41 | H | CSNHEt |
| 26 | H | CO-(3-$CF_3$-phenyl) | | | |
| 27 | H | $COCH_2$-(4-F-phenyl) | 42 | H | $CSNHPr^i$ |
| 28 | H | $CO(CH_2)_2$-(4-F-phenyl) | 43 | H | $CSNHBu^n$ |
| 29 | 4-AcO | COOEt | 44 | H | $CSNHBu^t$ |
| 30 | H | $COOPr^i$ | 45 | H | CSNHPh |
| 31 | H | $COO(CH_2)_2$-(4-Me-phenyl) | 46 | H | $CSNHCH_2Ph$ |
| 32 | H | $COO(CH_2)_3OMe$ | 47 | H | $CSNH.CH=CH_2$ |
| 33 | H | $CONHBu^t$ | 48 | H | $CSNH.CH\equiv CHCH_3$ |
| 34 | H | $CONHCH:CH_2$ | 49 | H | $CO.n-C_5H_{11}$ |
| 35 | H | $CONHCH:CH.CH_3$ | 50 | H | $CO.n-C_6H_{13}$ |
| 36 | 4-Cl | $CONHPr^n$ | 51 | H | $CO.n-C_7H_{15}$ |
| 37 | 4-Me | $CONHBu^n$ | 52 | H | CONHEt |

EXAMPLE 2

4-[4'-[2-(2,3-dihydrobenzo-1,4-dioxinyl]-4'hydroxybutylamino]-1-ethoxycarbonylpiperdine (54)

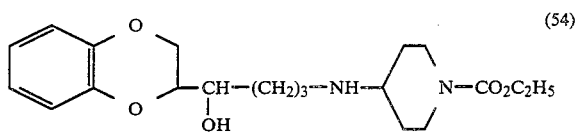
(54)

D56 (27 g) was dissolved in dry methanol (110 ml), and the solution neutralised to pH 7 by adding ethanolic HCl solution and cooled to room temperature. After adding 1-ethoxycarbonylpiperid-4-one (44 g), NaCNBH$_3$ (6 g) was added to the mixture under cooling and stiring, under nitrogen. After 0.5 hr, 3 Å molecular sieves were added and the mixture stirred at room temperature for 16 hr.

The resulting precipitate was filtered off under suction, washed with methanol, and the filtrate solvent was removed in vacuo.

The oily residue was extracted with diethyl ether at pH 7, and the aqueous layer at pH 14 was extracted twice with chloroform and washed with water.

After drying (Na$_2$SO$_4$) the extract was filtered and evaporated to dryness in vacuo crystallisation from diethyl ether yielded (54).

m.pt. 83° C. (ether).

| Analysis | C | H | N | O |
|---|---|---|---|---|
| Calc. for $C_{20}H_{30}N_2O_5$ | 63.47 | 8.00 | 7.47 | 21.13 |
| found | 63.54 | 8.06 | 7.50 | 21.15 |

Compound (55) of Table 3 was prepared analogously The compounds of Table 4 are prepared analogously.

TABLE 3

Structure: benzodioxane-CH(OH)-(CH₂)₃-NHA

| No. | A | % increase of voltage electro stimulation test dose 32 mg/kg i.d., 6 guinea pigs. |
|---|---|---|
| (54) | cyclohexyl-NCOOEt | 39.4 |
| (55) | cyclohexyl-NCONHPr$^n$ | 10.8 (16 mg/kg) |

TABLE 4

Structure: R-benzodioxane-CH(OH)-(CH₂)₃-NH-piperidine-NA

| No. | R | A |
|---|---|---|
| 56 | H | Me |
| 57 | H | Pr$^n$ |
| 58 | H | Ph |
| 59 | H | ―⌬―Me |
| 60 | H | COMe |
| 61 | H | COEt |
| 62 | H | COPr$^n$ |
| 63 | H | COPr$^i$ |
| 64 | H | CO―⌬―CF₃ |
| 65 | H | COCH₂Ph |
| 66 | H | COCH₂―⌬―F |
| 67 | H | CO(CH)₂―⌬―F |
| 68 | H | COOMe |
| 69 | 6-EtO | COOEt |
| 70 | H | COOPr$^n$ |
| 71 | H | COOPr$^i$ |
| 72 | H | COOBu$^n$ |
| 73 | H | COOCH₂Ph |

TABLE 4-continued

| No. | R | A |
|---|---|---|
| 74 | H | COO(CH₂)₂―⌬―Me |
| 75 | H | COO(CH₂)₂OMe |
| 76 | H | COO(CH₂)₃OMe |
| 77 | 6-Cl | CONHPr$^n$ |
| 78 | 6-M3 | CONHBu$^n$ |
| 79 | H | CONHEt |
| 80 | H | CONHPr$^i$ |
| 81 | H | CONHBu$^n$ |
| 82 | H | CONHBu$^t$ |
| 83 | H | CONH.CH:CH₂ |
| 84 | H | CONH.CH:CH.CH₃ |
| 85 | H | CONHPh |
| 86 | H | CONH―⌬―oMe |
| 87 | H | CONHCH₂Ph |
| 88 | H | CONH(CH₂)₂―⌬―oAc. |
| 89 | H | CSNHEt |
| 90 | H | CSNHPr$^n$ |
| 91 | H | CSNHPr$^i$ |
| 92 | H | CSNHBu$^n$ |
| 93 | H | CSNHBu$^t$ |
| 94 | H | CSNHCH₂Ph |
| 95 | H | CSNHCH₂Ph |
| 96 | H | CSNH.CH:CH₂ |
| 97 | H | CSNH.CH₂CH:CH₂ |
| 98 | H | CSNH.CH:CHCH₃ |

PHARMACOLOGY OF COMPOUNDS

Test Procedure to Demonstrate Antiarrythmic Effects

Electrostimulation Test

Method 1

According to the method by SZEKERES, L. and PAPP, G. J., (Naunyn-Schmiedebergs Arch. exp. Path. Pharmak. 245, 70 (1963), arrhythmias are induced in Guinea pigs by electrostimulation of the right ventricle of the heart. The animals are anesthetized with Urethane (1.2 g/kg i.p.) and artificially respired before a needle electrode is inserted in the right ventricle of the heart. Substances are given intraduodenally 30 min before the stimulation. The voltage needed for induction of extrasystoles in control animals (n=6) is compared with that required for induction of arrhythmias in treated animals (n=6). The difference is statistically evaluated by the unpaired t-test (STUDENT).

Method 2

Arrhythmias are elicited by serial electrical shocks (50 HZ impulse duration; 0.5 mins) applied to the right ventricle of guinea pig via needle electrodes. The therapeutic effects of test compounds are determined by infusing these compounds in the jugular vein at a solution concentration of 3 mg/ml and an infusion speed of 0.55 ml/min.

The results on compounds tested are shown in Tables IA, IB, IC and 3. In the tables * means statistically significant $p<0.01$.

Toxicity

No compound-induced toxic effects were observed in the above tests.

I claim:

1. A compound of the formula (I):

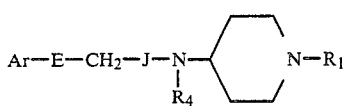

or a pharmaceutically acceptable acid addition or quaternary ammonium salt thereof,
wherein:
Ar is phenyl or naphthyl;
E is O or S:
J is $C_{3-5}$ polymethylene, substituted by one or two hydroxy groups optionally derivatised by nitrato, $C_{1-4}$ alkoxy, phenyl $C_{1-4}$ alkoxy or $C_{1-7}$ carboxylic acyloxy;
$R_1$ is $C_{3-8}$ alkanoyl or phenyl $C_{2-8}$ alkanoyl; a group $COR_2$ where $R_2$ is $C_{2-3}$ alkoxy, phenyl $C_{1-4}$ alkoxy or $C_{1-4}$ alkoxy $C_{3-4}$ alkoxy; or a group $CXNHR_3$ where X is O or S and $R_3$ is $C_{2-4}$ alkyl, $C_{2-4}$ alkenyl, phenyl or phenyl $C_{1-4}$ alkyl; and
$R_4$ is hydrogen or $C_{1-4}$ alkyl;
and wherein any phenyl or naphthyl moiety is optionally substituted by one or two substituents selected from halogen, $C_{1-4}$ alkyl, $C_{1-4}$ alkoxy, unsubstituted $C_{1-6}$ hydrocarbylcarbonyloxy, cyano and trifluoromethyl.

2. A compound according to claim 1 of formula (IA):

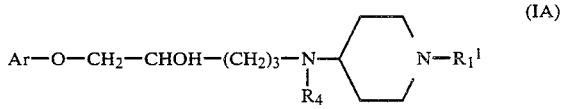

wherein:
$R_1{}^1$ is $C_{3-6}$ alkanoyl or phenyl $C_{2-6}$ alkanoyl; a group $COR_2$; or a group $CXNHR_3$; X, $R_2$ and $R_3$ being as defined in claim 1; and
Ar and $R_4$ are as defined in claim 1;
and wherein any phenyl or naphthyl moiety is optionally substituted as defined in claim 1.

3. A compound according to claim 1 of formula (IV):

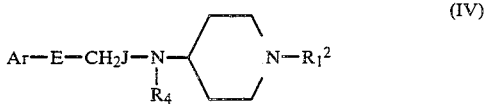

wherein:
$R_1{}^2$ is a group $COR_2$ or a group $CXNHR_3$ where X, $R_2$ and $R_3$ are as defined in claim 1; and the remaining variables are as defined in claim 1; and wherein any phenyl or naphthyl moiety is optionally substituted as defined in claim 1.

4. A compound according to claim 1 of formula (VI):

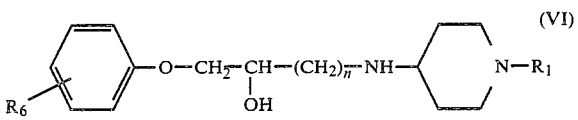

wherein:
$R_1$ is as defined in claim 1;
n is 2, 3 or 4; and
$R_6$ is hydrogen, halogen, $C_{1-4}$ alkyl, $C_{1-4}$ alkoxy, $C_{1-6}$ hydrocarbylcarbonyloxy, cyano or trifluoromethyl.

5. A compound according to claim 4 of formula (VII):

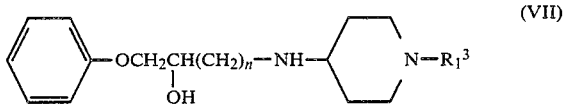

wherein:
$R_1{}^3$ is $C_{3-8}$ alkanoyl, $C_{2-3}$ alkoxycarbonyl or $CXNHR_3{}^1$ where $R_3{}^1$ is $C_{3-4}$ alkyl and X is O or S; and
n is as defined in claim 4.

6. A compound according to claim 5, of formula (VIII):

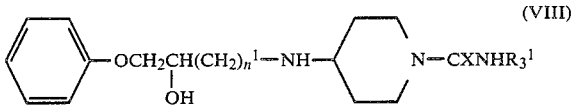

wherein:
$n^1$ is 2 or 3; and
$R_3{}^1$ is as defined in claim 5.

7. A compound according to claim 1 which is:
4-(5-phenoxy-4-hydroxypentylamino)-1-n-propylaminocarbonylpiperidine,
4-(5-phenoxy-4-hydroxypentylamino)-1-n-propylaminothiocarbonylpiperidine,
4-(4-phenoxy-3-hydroxybutylamino)-1-n-propylaminocarbonylpiperidine,
4-(6-phenoxy-5-hydroxyhexylamino)-1-n-propylaminocarbonylpiperidine,
4-(5-phenoxy-4-hydroxypentylamino)-1-n-butylaminocarbonylpiperidine,
4-(5-phenoxy-4-hydroxypentylamino)-1-n-butylcarbonylpiperidine,
4-(5-phenoxy-4-hydroxypentylamino)-1-isopropylaminocarbonylpiperidine, or
4-(4-phenoxy-3-hydroxybutylamino)-1-isopropylaminocarbonylpiperidine, or a pharmaceutically acceptable acid addition or quaternary ammonium salt thereof.

8. A pharmaceutical composition for the treatment of cardiac arrhythmia comprising a cardiac antiarrhythmic effective amount of a compound according to claim 1, or a pharmaceutically acceptable acid addition or quaternary ammonium salt thereof, together with a pharmaceutically acceptable carrier.

9. A method of treatment or prophylaxis of cardiac arrhythmias in mammals comprising the administration to the sufferer of a cardiac antiarrhythmic effective amount of a compound according to claim 1 or a pharmaceutically acceptable acid addition or quaternary ammonium salt thereof.

* * * * *